United States Patent [19]

Morgan, Jr. et al.

[11] Patent Number: 5,151,266

[45] Date of Patent: Sep. 29, 1992

[54] USE OF ANIONIC DETERGENTS WITH CONJUGATES OF MONOCLONAL OR POLYCLONAL ANTIBODIES

[75] Inventors: A. Charles Morgan, Jr.; Gowsala Pavanasasivam, both of Edmonds, Wash.

[73] Assignee: NeoRx Corporation, Seattle, Wash.

[21] Appl. No.: 291,420

[22] Filed: Dec. 22, 1988

Related U.S. Application Data

[63] Continuation of Ser. No. 767,493. Aug. 20, 1985, abandoned.

[51] Int. Cl.$^5$ ............................................. A61K 39/395
[52] U.S. Cl. ................................. 424/85.8; 424/85.91; 530/387.1; 530/388.1; 530/388.8; 530/390.1; 530/391.7; 530/392; 530/393; 530/403; 530/405; 530/422; 530/828; 530/861; 514/2; 514/8; 514/21; 514/937; 514/975; 252/351
[58] Field of Search ............... 530/387, 388, 389, 391, 530/403, 405, 402, 422, 424, 425; 924/85.8, 85.91; 514/2, 8, 21

[56] References Cited

U.S. PATENT DOCUMENTS

| | | | |
|---|---|---|---|
| 3,607,858 | 9/1971 | Querry et al. | 514/2 |
| 4,452,903 | 6/1984 | Lee et al. | |
| 4,454,232 | 6/1984 | Breglio et al. | |
| 4,609,707 | 9/1986 | Nowinski et al. | 524/54.1 |
| 4,639,425 | 1/1987 | Baier | |
| 4,668,639 | 5/1987 | Johannsson | 436/518 |

FOREIGN PATENT DOCUMENTS

2033081A  5/1980  United Kingdom.

OTHER PUBLICATIONS

A. Helenius and K. Simons, "Removal of Lipids from Human Plasma Low-Density Lipoprotein by Detergents", *Biochemistry* 10: 2542-2547, 1971.
Morgan, A. C. Jr. et al, *Monoclonal Antibodies and Cancer Therapy* Alan R. Liss, Inc., N.Y. USA (1985), pp. 237-242. Biosis Abstract 86:182441.
Schrof, R. W. et al, J. Nuc. Med. 26(4): 437 (1985) cited in Biosis Abstract 85:209858.
Morgan, A. C. Jr. et al., J. Cell. Biochem. (1985) 9 Part A; p. 53, cited in Biosis Abstract 85:123216.
Crumpton, M. J. et al, FEBS Lett. 22(2): 210-212 (1972) cited in Chem. Abstract CA77(3):17767t.
Riley, R. L. et al, Immunochemistry, 14(3): 221-5 (1977) cited in Chem. Abstract CA87(11):82966c.
P. E. Thorpe et al., "The Preparation and Cytotoxic Properties of Antibody-Toxin Conjugates", *Immunol. Rev.* 62:119-158, 1982.
F. K. Jansen et al., "Immunotoxins: Hybrid Molecules Combining High Specificity and Potent Cytotoxicity", *Immunol. Rev.* 62: 185-216, 1982.
A. Helenius et al., "Properties of Detergents", *Meth. Enzymol.* 56:734-749, 1979.
C. Tanford et al., "Characterization of Membrane Proteins in Detergent Solutions", *Biochim. Biophys. Acta* 457:133-170, 1976.
A. Helenius et al., "Solubilization of Membranes by Detergents", *Biochim. Biophys. Acta* 415:29-79, 1975.

*Primary Examiner*—Esther L. Kepplinger
*Assistant Examiner*—Jeff Kushan
*Attorney, Agent, or Firm*—Seed and Berry

[57] ABSTRACT

Methods are disclosed for increasing the solubility of antibodies and their radioisotope, toxin, or drug immunoconjugates and for reducing the non-specific uptake of antibody, either conjugated or unconjugated, into the RES organs such as via Fc receptor-mediated mechanisms. The methods involve incubation of the reactive component with amphipathic molecules, such as an anionic detergent, to achieve the desired result. A preferred anionic detergent in this regard is sodium dodecylsulfate.

43 Claims, 1 Drawing Sheet

USE OF ANIONIC DETERGENTS WITH CONJUGATES OF MONOCLONAL OR POLYCLONAL ANTIBODIES

CROSS-REFERENCE TO RELATED APPLICATION

This application is a continuation of U.S. application Ser. No. 767,493, filed Aug. 20, 1985, now abandoned under C.F.R. Section 1.62.

DESCRIPTION

1. Technical Field

The present invention relates to the use of amphipathic molecules in general, and more specifically, to the use of amphipathic molecules, such as anionic detergents, to increase the solubility of immunoconjugates of toxins, radioisotopes and drugs, and to decrease the non-specific uptake of monoclonal antibodies, either conjugated or unconjugated.

2. Background Art

The use of monoclonal antibodies as targeting or delivery vehicles has, in recent years, prompted the emergence of a variety of novel anti-cancer strategies. Among these strategies is serotherapy using unconjugated antibodies, as well as the conjugation of antibodies with radioisotopes, drugs, or toxins, resulting in what are known as "immunoconjugates." There are several methods for coupling these agents to antibodies; one commonly used for toxins, for example, involves the introduction of disulfide groups into the antibody and sulfhydryl groups into the toxin followed by the formation of a covalent disulfide bond, to form an "immunotoxin." These modifications usually increase the hydrophobicity of the conjugates and promote their aggregation and even precipitation. Despite attempts to control the degree of substitution of the antibody, the conjugates are often unstable upon storage and precipitate spontaneously, resulting in decreased potency, stability and therapeutic efficacy. Traditionally, the only way to control the solubility of immunoconjugates was to control the degree of substitution of the heterobifunctional ligand. This technique, however, has the major drawback of also limiting the amount of toxin that can be conjugated to the antibody, and is inconsistent in the substitution of functional groups, such as lysine, in both antibody and toxin. In addition, certain unconjugated antibodies, such as antibodies of the $IgG_3$ subclass, are poorly soluble once purified from either ascites or spent culture medium. As an isolated antibody preparation, they can spontaneously precipitate upon storage at 4° C. or upon reconstitution from $-70°$ C. This subclass of antibody would then produce highly insoluble and unstable immunotoxins. Although there are many different methods of coupling drugs, isotopes and toxins to antibodies, most have similar problems of solubility.

A further problem exists in the preparation of immunotoxin conjugates. For example, the most commonly used toxins comprise two polypeptide chains, denoted A and B, that are linked by a disulfide bond. The toxins bind via a recognition site on the B-chain to receptors on the cell surface, and the A-chain then penetrates (or is translocated across) the cell membrane into the cytosol where it inhibits protein synthesis. While most immunotoxins are constructed using A-chain alone coupled to specific antibodies, the use of intact toxin for immunotoxin preparations has a number of potential advantages. Intact toxin conjugates typically have a higher potency than do conjugate preparations made with A-chain alone. This is because the B-chain performs a vital role in internalization of immunotoxin, a limiting factor for immunoconjugate potency. In essence, increased internalization translates into increased potency. In addition, preparation of immunotoxins is more difficult if one has to separate A-chain from B-chain before attempting to prepare the conjugate. This typically involves an affinity purification step and a step in which the bond between A-chain and B-chain is reduced in order to cleave the intermolecular disulfide bond. Approaches to making intact toxin preparations that could retain selective potency against antigen-positive cells have been limited. Thorpe, et al. (*Immun. Rev.* 62:119–158, 1982) demonstrate that selective immunoconjugates can be formed with intact toxin conjugated with antibody. By simply conjugating intact toxin via N-succinimidyl-3-(2-pyridyldithio)propionate (SPDP) to antibody, a certain percentage of the immunotoxin molecules have occluded B-chains that cannot bind to carbohydrate and therefore cannot mediate toxicity to non-antigen-bearing tumor cells or normal cells. Conjugate molecules with B-chains that still retain the ability to bind to carbohydrate can be removed by affinity chromatography. However, even after depletion, certain immunotoxin preparations frequently still have a high degree of nonspecificity and toxicity. The reason for this is unclear.

In addition to the problems of solubility and toxicity of immunoconjugates, nonspecific uptake of the monoclonal antibodies and their conjugates into the reticuloendothelial system (RES) organs, e.g., the lung, liver, spleen, and bone marrow has limited their potential efficacy and diminished the therapeutic index when used in vivo. RES elements are also present in many other tissues, including lymph nodes, tonsil and intestine. Fc receptors may account for a major portion of the nonspecific uptake of monoclonal antibodies and their conjugates into the RES organs Other systems such as C3b or C3d receptors, immune complex receptors and carbohydrate or glycoprotein receptors may also participate in non-specific uptake of antibody. As already demonstrated receptors for carbohydrate also bind residues on the toxin molecule that can enhance nonspecific uptake of the immunoconjugate.

Currently, enzymatic fragmentation of antibody is the standard technique for decreasing Fc receptor-mediated uptake. However, this method has several drawbacks for both radiolabeled antibody preparations and immunoconjugate preparations First, enzymatic cleavage of the Fc portion of the antibody is a process that is, from a regulatory and quality-control standpoint, difficult to accomplish since one has to test for residual enzyme in antibody preparations. Second, it has been well documented that F(ab')2 fragments have increased degradation rates compared to intact antibodies, and third, the use of an F(ab)[1] or Fab (monovalent fragment of antibody) can have an additional drawback in that the affinity for the antigen is greatly reduced due to the fact that the antibody is binding via only one binding site. In addition, ligand substitution onto fragments of antibody is more limited than with whole antibody and increases the likelihood of substitution into the antigen combining site that would decrease the fragment's immunoreactivity. There have been few studies that have demonstrated a consistent increase in tumor uptake or a decrease in RES organ accumulation with fragments compared to intact antibody.

Another problem frequently encountered with purified preparations of monoclonal antibody is endotoxin contamination. Endotoxin in some cases co-purifies with the antibody and thus appears to be bound to the monoclonal antibody. Conventional affinity procedures to isolate endotoxin from the antibody in these cases are not successful, because removal of the endotoxin also removes the antibody. Thus, these contaminated antibody preparations cannot be utilized in patients because the endotoxin causes fevers and even shock.

Consequently, there is a need in the art for (a) a more effective means of increasing the solubility of immunoconjugates after the addition of linkers or cytotoxins to antibodies; (b) a method of substantially inhibiting the uptake of antibody and antibody conjugates onto Fc and other receptors, and thus into the RES organs; (c) a method of reducing the toxicity of intact toxin immunoconjugates; and (d) a method of reducing the levels of endotoxin contaminating antibody preparations without significantly affecting the recovery of antibody. The present invention fulfills these needs, and further provides other related advantages.

Disclosure of Invention

Briefly stated, the present invention relates to methods for increasing the solubility of immunoconjugate preparations and for reducing the uptake of antibody (either conjugated or unconjugated) into the RES organs via receptor-mediated mechanisms, through the use of amphipathic molecules, such as anionic detergents.

In particular, the present invention discloses a method for increasing the solubility of immunoconjugate preparations comprising incubating the immunoconjugate preparation with amphipathic molecules in an amount sufficient to increase the solubility of the preparation. In accordance with a preferred embodiment, the amphipathic molecules constitute an anionic detergent, such as sodium dodecylsulfate (SDS). A related aspect of the present invention is concerned with a method for increasing the solubility of unconjugated immunoglobulin comprising incubating the immunoglobulin preparation with amphipathic molecules, such as an anionic detergent, in an amount sufficient to increase the solubility of the immunoglobulin preparation. In one embodiment of the present invention, the immunoglobulin preparation is a member of the murine subclass IgG$_3$.

A third aspect of the present invention discloses a method for reducing the binding of antibody to receptors, comprising incubating the antibodies with amphipathic molecules, such as an anionic detergent, in an amount sufficient to reduce the binding of the antibody to receptors without altering its binding to target antigen.

Another aspect of the present invention discloses a method for reducing the toxicity of intact toxin conjugates, comprising incubating the toxin conjugate with amphipathic molecules, such as an anionic detergent in an amount sufficient to reduce the toxicity of the intact toxin conjugate.

Yet another aspect of the present invention is directed toward a method for reducing the level of endotoxin in monoclonal antibody preparations, comprising incubating the monoclonal antibody preparation with amphipathic molecules, such as an anionic detergent, in an amount sufficient to reduce the level of endotoxin in the preparation.

Other aspects of the present invention will become evident upon reference to the following detailed description and attached drawing.

BRIEF DESCRIPTION OF THE DRAWINGS

The FIGURE depicts flow cytometry profiles of treated, untreated and F(ab')$_2$ fragments of a monoclonal antibody 9.2.27 to a human melanoma associated antigen and their binding to Fc receptors on human peripheral monocytes. Panel 1A graphically illustrates the binding of untreated monoclonal antibody 9.2.27 to monocytes. Panel 1B graphically illustrates non-Fc-mediated binding of untreated 9.2.27 F(ab')$_2$ fragments to monocytes. Panel 1C graphically illustrates the binding of FITC-labeled goat anti-mouse antibody ("GAM*FITS") to monocytes in the absence of monoclonal antibody 9.2.27. Panel 1D graphically illustrates the binding of monoclonal antibody 9.2.27 treated with 1% SDS to monocytes. Panel 1E graphically illustrates the binding of monoclonal antibody 9.2.27 treated with 0.1% SDS to monocyte. The mean channel fluorescence intensity is shown as 209, 121, 87, 128 and 148 for Panels 1A to 1E, respectively.

BEST MODE FOR CARRYING OUT THE INVENTION

Figure 1A:
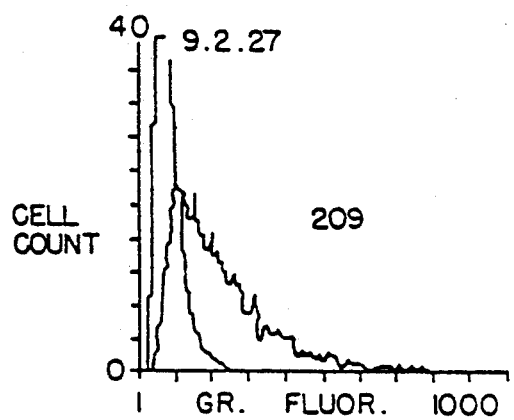

Prior to setting forth the invention, it may be helpful to an understanding thereof to set forth definitions of certain terms to be used hereinafter.

Immunoconjugate: A covalent conjugate of a monoclonal or polyclonal antibody together with a plant, fungal, or bacterial toxin or the A-chain thereof, a ribosomal inactivating protein, a drug directly bound or indirectly bound through a carrier molecule to antibody, a ligand for radioisotopes, a biological response modifier that can indirectly or directly activate cytotoxic mechanisms, or other cytotoxic agents.

Anionic Detergent: A negatively charged detergent with a nonpolar hydrocarbon end that is soluble in oil, lipid or organic solvents, and a polar end that is soluble in aqueous solutions, or a similar amphipathic molecule.

The concept of targeting specific cell lysis by antibodies to tumors by passive immunotherapy has generated interest for almost a century. However, the capacity of antibodies to destroy tumors in animals or man has always been limited. As a result, a series of attempts have been made to render the effector function of antibodies more potent by attaching anticancer agents to these antibodies, first described by Mathe, et. al. (C.R. Acad. Sci. (Paris) 246:1626, 1958); toxins, as initiated by Moolten and Cooperband (Science 169:68, 1970); and radioisotopes or enzymes (Ghose, et. al., *Ann. N.Y. Acad. Sci.* 277:671, 1976; Ghose and Blair, *J. Natl. Cancer Inst.* 61:657, 1978). Higher potency, however, is only beneficial for tumor therapy if it is specific for the target tissue, in the sense that the toxic agent conjugated to antibody remains inactive during transport in the body and becomes activated only after binding of the antibody to the target cells.

While significant progress has been made toward successfully attacking tumor cells through the use of cytotoxic agents covalently linked to specific antibodies, (Jansen et. al., *Immunological Rev.* 62:186, 1982; Thorpe and Ross, *Immunological Rev.* 62:119, 1982), the therapeutic use of immunoconjugates is still problematic. For example, while the use of intact toxins requires less manipulation of the toxin molecule and provides increased potency against target cells, nonspecific binding of the B-chain of the toxin, through presumably hydrophobic domains, has heretofore made the in vivo delivery of intact toxin conjugates not feasible for all antibodies. This latter problem may be a function of the antibody used for conjugation since some investigators report toxic intact toxin conjugates while others report non-toxic ones. In the hands of the inventor, one antibody, 9.2.27 ($\gamma$2a subclass) forms non-toxic conjugates with intact abrin while the D3 MAb ($\gamma$1 subclass) to the L10 hepatocellular carcinoma forms conjugates with intact abrin that are highly toxic to normal tissues. This toxicity can be abrogated with SDS. While the B-chain may be removed, and A-chain alone coupled to monoclonal antibodies, the absence of B-chain usually results in decreased potency of the immunotoxin.

As noted above, there are several other problems in the in vivo application of immunocongugates, including the nonspecific uptake of the antibodies into the RES organs via other forms of binding, such as to Fc receptors, and the tendency of immunoconjugates during storage to lose solubility and spontaneously precipitate, resulting in decreased potency and therapeutic effectiveness. Through the use of amphipathic molecules such as anionic detergents, however, the present invention effectively ameliorates the aforementioned problems.

In the present invention, amphipathic molecules, such as anionic detergents are used to (a) increase the solubility of immunoconjugate preparations; (b) increase the solubility of unconjugated immunoglobulin preparations; (c) reduce the binding of antibody to Fc receptors; (d) reduce the toxicity of intact toxin conjugates; and (e) reduce the level of endotoxin in monoclonal antibody preparations.

Within the present invention, a variety of anionic detergents may be utilized, including sodium dodecylsulfate (sodium lauryl sulfate), cetyl ammonium sulfate, and taurcholic acid. A particularly preferred anionic detergent is sodium dodecylsulfate (SDS). A listing of other anionic detergents which may be suitable within the present invention is found within *McCutcheon's Emulsifiers and Detergents*, MC Publishing, Glen Rock, N.J. Anionic detergents are generally characterized by a large non-polar hydrocarbon end, and a polar end, such as SDS, which has the general structural formula:

$$CH_3-(CH_2)_{(n)}-SO_3^- \ Na^+$$

Anionic detergents, such as SDS, are believed to bind both to positively charged groups (i.e., $\gamma$amino group of lysines) and to the hydrophobic regions of proteins. It is presumably these hydrophobic domains that are partially responsible for nonspecific binding of the B-chain to non-antigen positive cells or for binding of antibodies to Fc receptors.

Further, increased hydrophobicity imparted by conjugation contributes to aggregation and precipitation of the resulting immunoconjugate. SDS, through its interaction with hydrophobic regions, presumably reduces self-association of molecules, thereby decreasing aggregation of the preparation.

Within each of the methods described above, it is necessary to incubate the antibody preparation with an amphipathic molecule such as an anionic detergent to achieve the desired result. A preferred detergent concentration is between 0.01% and 1% by weight to volume (w/v). In addition, incubation conditions of approximately room temperature (25° C.) or 37° C. for 30–60 minutes are preferred. Particularly preferred time and temperature combinations include incubation at 37° C. for approximately 30 minutes and incubation at 25° C. for a period of approximately one hour. It is also preferable to remove non-antibody bound anionic detergent such as by crystallization at 4° C., by gel filtration or by passage over albumin-Sepharose. The latter method is the most efficient at separating free SDS from that bound to antibody with >90 percent recovery of antibody.

The preferred methods for increasing the solubility of immunoconjugate preparations and reducing nonspecific uptake into RES organs are those initiated after coupling of antibody and cytotoxin. As noted above, these methods involve incubation of the immunoconjugate with an anionic detergent at a concentration between 0.01% and 1% (w/v) SDS. The immunoconjugate preparation is typically 1 mg/ml, although lower and higher concentrations may be utilized. More specifically, the immunoconjugate preparation is treated at a relatively high concentration in a small volume, for appropriate dilution later, i.e., if the immunoconjugate preparation is present as a 1 mg/ml solution, then 1 ml is treated with 10 ul of a 10% solution of SDS. After mixture, the antibody is allowed to stand either at 37° C. or room temperature for the preferred incubation time. The maximum concentration of immunocytotoxin that could be successfully treated at 25° C. was found to be 10 mg/ml. Above this concentration, the antibody cytotoxin preparation generally loses solubility upon treatment with SDS at 25° C., but not at 37° C. One important feature of this treatment is that it involves only a short exposure to the detergent. The incubation time is typically 30–60 minutes and the temperature of incubation either room temperature (25° C.) or 37° C.

After treatment, non-antibody bound SDS is removed by the aforementioned methods. The first is a crystallization step in which the solution is chilled at 4° C. which causes the crystallization of excess SDS. The supernatant is removed and used as is, or applied to a G-25 column to further separate the low molecular weight SDS from immunoconjugate. Alternatively, the SDS treated antibody can be adsorbed to albumin-Sepharose and the non-adsorbed antibody recovered. If preferred, the residual SDS remaining bound to protein or free can be determined by binding with acridinine orange and solubilization in toluene.

The SDS appears to be stably bound to antibody since passage over albumin-Sepharose removes only free SDS, not SDS bound to antibody, and because inhibition of RES uptake of antibody can occur in vivo, even after circulating in serum where SDS could presumably be competed for by a variety of different proteins.

Treatment with SDS can be performed with either unconjugated or conjugated monoclonal antibody preparations. In the latter case, the immunoconjugate preparation can either be present as a soluble preparation, i.e., a supernatant from an ultracentrifugation step (100,000$\times$g for 60 minutes) or can be present as a spontaneously precipitated immunoconjugate preparation. Spontaneous precipitation occurs oftentimes in conjugating with SPDP, or other hetero-bifunctional linkers, and results from over-conjugation, i.e., exposure for long periods of time or high concentrations of the agent. These insoluble precipitates can be treated with SDS and returned to solubility once again. More importantly, the SDS will render the immunoconjugate preparation consistently soluble, i.e., upon storage at 4° C., immunoconjugate preparations will remain soluble and not gradually precipitate with time, which is common with untreated immunoconjugate.

Further, it has been determined that with drug conjugates, over-derivatized antibody or antibody bound to carriers like poly-L-lysine can be returned to solubility by the use of SDS. This is particularly relevant with drugs such as adriamycin, which seems to impart a high degree of hydrophobicity to the antibody-drug conjugate. In the case of both toxin conjugates and drug conjugates, resultant testing for potency seems to indicate little loss of activity after SDS treatment, and no loss of antigen specificity or antigen selectivity in killing antigen positive cells.

In addition, it was determined that SDS could be used to solubilize unconjugated antibody as well. For instance, the $IgG_3$ subclass of antibody is poorly soluble once isolated from either ascites or spent culture medium. As an isolated antibody preparation, it spontaneously precipitates upon storage at 4° C. or at −70° C. However, through the use of SDS as described herein, the solubility of this particularly unstable subclass is enhanced. In addition, short exposure to SDS seems to have little effect on immunoreactivity of this unconjugated antibody subclass.

To summarize the examples which follow, Example I demonstrates the effect of a suitable anionic detergent on immunoreactivity. Example II demonstrates the use of an anionic detergent to inhibit Fc receptor-mediated binding and to reduce nonspecific RES uptake. Example III demonstrates the use of an anionic detergent to reduce the in vivo toxicity of intact toxin conjugates. Example IV demonstrates the use of an anionic detergent to reduce the level of endotoxin in monoclonal antibody preparations.

The following examples are offered by way of illustration and not by way of limitation.

EXAMPLE I

Effect of Anionic Detergent on Immunoreactivity

This example demonstrates that incubation of immunoglobulins or immunoconjugates with an anionic detergent to improve solubility does not substantially effect the ability of antibody to bind to antigen. As shown in Table I, SDS was added to unconjugated antibody (1 mg/ml) in the indicated amounts for the indicated times and then free SDS removed by centrifugation on a 0.5 ml minicolumn of G-25. Antibody was then assayed for binding to melanoma cells at 0.1 ug $10^5$ cells. Fluorescent- labeled anti-flow immunoglobulin was added, and the cells were examined by flow cytometry. The mean fluorescence intensity of melanoma cell binding was determined for SDS-treated and untreated antibody preparations. The mean fluorescence intensity was compared and calculated as a percentage of the amount of binding of untreated antibody to melanoma cells.) There was insignificant inhibition of binding below 0.2% at 25° C. or 0.1% at 37° C. incubation.

TABLE I

| Percent | Exposure Time | | | | |
|---|---|---|---|---|---|
| | 5' | 15' | 30' | 60' | |
| 1 | 72* | 70 | 50 | 36 | 25° C. |
| 0.5 | 56 | 67 | 83 | 74 | |
| 0.2 | 79 | 78 | 84 | 89 | |

TABLE I-continued

| Percent | Exposure Time | | | | |
|---|---|---|---|---|---|
| | 5' | 15' | 30' | 60' | |
| 0.1 | 88 | 88 | 84 | 86 | |
| 0.05 | 95 | 98 | 94 | N.T. | |
| 0.01 | 104 | 104 | 99 | 102 | |
| 1 | 62 | 44 | 39 | 23 | 37° C. |
| 0.5 | 72 | 79 | 38 | 28 | |
| 0.2 | 70 | 77 | 78 | 62 | |
| 0.1 | 98 | 89 | 91 | N.T. | |
| 0.05 | 100 | 96 | 101 | 97 | |
| 0.01 | 101 | 102 | 101 | 102 | |

*percent of control

EXAMPLE II

SDS-Mediated Inhibition of Fc-Receptor Binding and RES Uptake

Figure 1B:
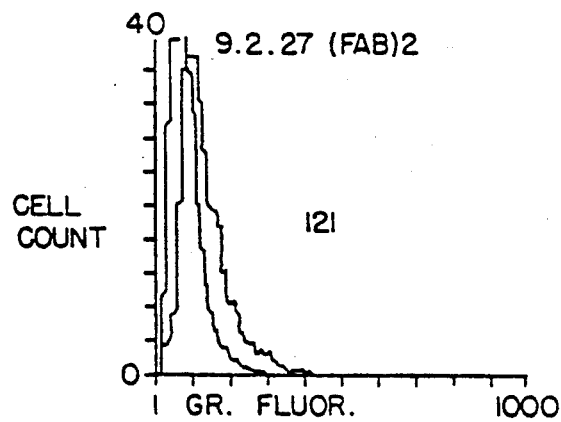
Figure 1C:
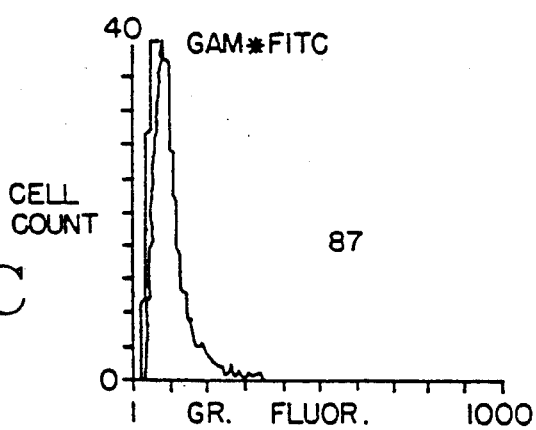
Figure 1D:
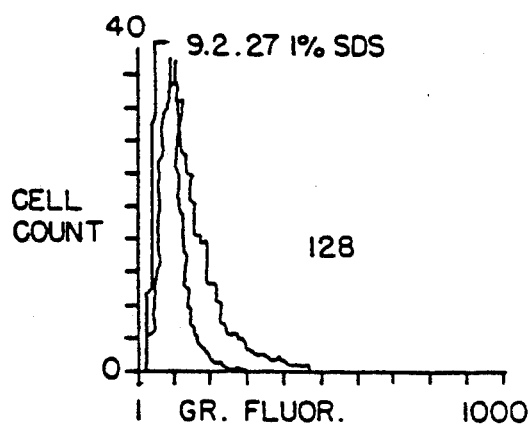
Figure 1E:
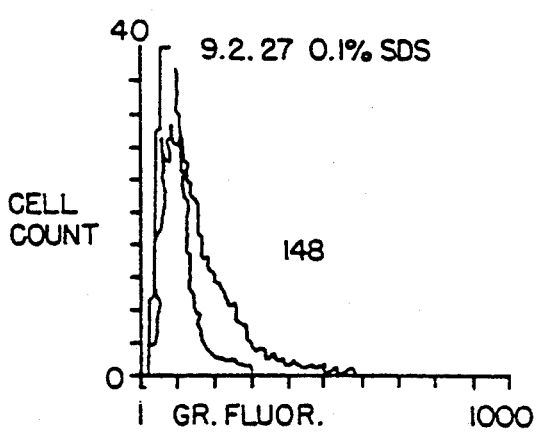

Incubation of anionic detergent with antibody inhibited Fc receptor-mediated binding to cells, as depicted in FIG. 1. As described above, Fc receptor binding may also play a significant role in nonspecific RES uptake. As shown in Table II, detergent treatment of antibody preparations decreased the amount of nonspecific antibody uptake into the RES tissues, liver and spleen.

A. Diminution of Fc receptor-mediated binding

Detergent-treated antibody, untreated antibody, and F(ab')₂ fragments were incubated with human monocytes and analyzed by flow cytometry. Cultured human monocytes express a well documented Fc receptor for murine monoclonal antibodies. Treatment of a monoclonal antibody 9.2.27, which is an $IgG_{2a}$ antibody, with concentrations of SDS as low as 0.1% effectively reduced the binding to Fc receptors to the level that was seen with control F(ab')₂ preparations. (FIG. 1).

Monoclonal antibody 9.2.27 (mouse anti-human melanoma) was incubated with 0.1% or 1% (w/v) SDS for 30 min at 25° C. SDS-treated antibody (0.1 ug) was incubated with $5 \times 10^5$ human elutriated monocytes (>95% purity) for 30 min at 4° C. Untreated 9.2.27 and F(ab')₂ fragment of 9.2.27 served as controls. The monocytes were washed twice, incubated with FITC-labeled goat anti-mouse F(ab)₂ and analyzed by flow cytometry. FIG. 1 demonstrates that incubation of monoclonal antibody 9.2.27 with 0.1% or 1% SDS produces an antibody-binding profile very similar to that of 9.2.27 F(ab')₂ fragments. These data indicate that treatment of antibody with SDS substantially inhibits Fc receptor-mediated binding to human monocytes.

B. Reduction of Nonspecific RES Uptake

The reduction in binding activity demonstrated in (A) above was examined further to determine if the in vitro results would incicate reduced non-specific uptake in nude mice bearing human melanoma xenografts. As shown in Table II, the nonspecific uptake of 1% SDS-treated antibody in vivo was diminished in comparison to untreated antibody. Localization to the tumor site, however, was equivalent with the two antibody preparations, perhaps because of loss of some immunoreactivity after treatment with SDS (see Table I). Further experiments with reduced levels of SDS (0.1%) show enhancement of tumor uptake. Additional experiments have shown as little as 0.01% is sufficient to inhibit RES uptake.

TABLE II

Effect of SDS on Unconjugated Antibody Biodistribution In Vivo

| Tissue | % Inhibition With SDS |
| --- | --- |
| Spleen | 52.5 |
| Liver | 50.0 |
| Lung | −14.3 |
| Kidney | 33.3 |
| Muscle | 33.3 |
| Thyroid | −48.1 |

The procedure was as follows: 250 micrograms of $^{125}$I-labeled (Chloramine-T) antibody was incubated with 1% (w/v) SDS for 30 min at 25° C. SDS-treated radioiodinated antibody was administered intravenously to rodents at 50 ug/animal. Control animals received the same dose of ntreated $^{125}$I-labeled antibody intravenously. There was no difference in serum half-life between detergent-treated and untreated antibody preparations ($T_{\frac{1}{2}}=24$ hours). The rodents were sacrificed 48 h post-immunization, and the radiolabel associated with various tissues analyzed. The percent recovered dose was calculated as the percent of the total recovered cpm per gram of selected tissue. The percent inhibition with SDS treatment was calculated by the following formula:

$$\left( \frac{\text{percent recovered dose in tissue for untreated antibody}}{\text{percent recovered dose in tissue for SDS-treated antibody}} - 1.00 \right) \times 100$$

As demonstrated in Table II, SDS treatment of antibody significantly inhibited nonspecific uptake of antibody into RES tissues. No inhibition was seen in lung and thyroid, two sites of deiodination. The cpm in these tissues might primarily be free label not antibody associated. (Shown in Table III are the results of treatment of an immunotoxin on biodistribution in vivo). Shown is an intact abrin-9.2.27 conjugate; however similar results were achieved with a pokeweed antiviral protein conjugate of 9.2.27. In both of these cases, the uptake of the immunotoxin preparations was decreased in the RES organs compared to the untreated immunotoxin preparations.

The non-specific uptake of intact toxin conjugates can be effectively reduced by incubating the conjugates (which are devoid of ability to bind to carbohydrate via specific B-chain receptors) with SDS prior to passive therapy. Briefly, 131I-labeled monoclonal antibody 9.2.27 was conjugated using SPDP to $^{125}I$-labeled intact abrin. Intact toxin conjugates that retained B-chain binding via carbohydrates were removed by adsorption on galactose/Sepharose. The remaining intact toxin conjugates were incubated with 0.5% (w/v) SDS for 30 min at 25° C. Untreated and SDS-treated intact toxin-immunoconjugates were intravenously administered to nude mice at 50 ug/animal. There was no difference between serum half-life of control and detergent-treated intact toxin conjugates ($T\frac{1}{2}=3.5$ h). The rodents were sacrificed 24 h post-immunization, and various tissues were removed and assayed for associated radiolabel. As shown in Table III, incubation of intact toxin conjugates with SDS prior to in vivo administration results in a marked decrease in nonspecific uptake into RES tissues.

TABLE III

| Effect of SDS on Immunotoxin Biodistribution In Vivo | |
|---|---|
| Tissue | % Inhibition With SDS |
| Spleen | 37 |
| Liver | 52 |
| Lung | 27 |
| Kidney | 54 |
| Muscle | 0 |
| Thyroid | −25 |

EXAMPLE III

Reduction of In Vivo Toxicity of Intact Toxin Conjugates

The D3 (MAb to L10 hepatocellular carcinoma of guinea pigs) was conjugated to intact abrin via SPDP as above. After depletion over galactose-sepharose, conjugates were tested in vitro versus antigen positive and negative cells. There was a 10,000 fold difference in killing of antigen positive versus negative cells ($ID_{50}$ versus antigen positive cells $=10^{-14}$ M, $ID_{50}$ versus antigen negative cells $=10^{-10}$ M). A typical A/chain conjugate of D3 was $10^{-10}$ and $10^{-7}$ M $ID_{50}$ respectively. Guinea pigs (350 grams body weight) were injected with the D3-intact abrin conjugate at 1 and 10 ug doses/guinea pig. Both sets of animals died by 24 hours. After treatment with 0.5% SDS and removal of free detergent, the conjugate was administered in 3 doses of 150 ug each, three days apart (cumulative dose of 450 ug in 7 days). Guinea pigs were observed for 200 days and had no apparent toxicity.

EXAMPLE IV

Reduction in the Level of Endotoxin in MAb Preparations

Incubation of monoclonal antibodies with anionic detergent results in a decrease in endotoxin contamination of antibody preparations, as shown in Table IV. Monoclonal antibody (at two protein levels) purified from tissue culture supernates by Protein A Sepharose chromatography was assayed for endotoxin using the QCL limulus lysate test (Whittaker/MA Bioproducts). Equivalent results were obtained with an agglutination assay (Pyrotel, Woods Hole, Mass.) and shown to have endotoxin contamination. Antibody preparations were then incubated with 0.1% SDS at 37° C. for 30 min. Excess SDS was crystallized by chilling at 4° C. for 2 h and was removed by centrifugation at 2000×g for 10 min. An acridine orange binding assay determined that 494 ug of SDS remained bound per mg of antibody. Detergent-treated antibody showed a >95% reduction in endotoxin levels. A control experiment was performed using a detergent-treated antibody preparation purified from ascites which did not contain endotoxin. SDS treatment had no effect on the assessment of an endotoxin positive control.

TABLE IV

| Effect of SDS on Endotoxin Levels of MAb 9.2.27 | | | |
|---|---|---|---|
| | Before | After | Percent Reduction |
| 50 ug treated lot #407033 | 76 | 1.4 | 98.0 |
| 500 ug treated lot #411271 | 240 | 11.0 | 95.4 |

We claim:

1. A method for increasing the solubility of an immunoreactive immunoconjugate preparation without substantially affecting the immunoreactivity of the preparation, comprising:
incubating the immunoreactive immunoconjugate preparation with ananionic detergent at a concentration between about 0.01% and 1% by weight to volume; and
removing substantially any unbound anionic detergent.

2. The method of claim 1 wherein said anionic detergent is sodium dodecylsulfate.

3. The method of claim 2 wherein said immunoconjugate preparation is present in a concentration of approximately 1 mg/ml.

4. The method of claim 2 wherein said immunoconjugate preparation is incubated for 30–60 minutes.

5. The method of claim 4 wherein the step of incubation is carried out at 25° C. or 37° C.

6. The method of claim 2 wherein the step of incubation is carried out at 37° C. for a period of approximately 30 minutes.

7. The method of claim 2 wherein the step of incubation is carried out at 25° C. for a period of approximately one hour.

8. The method of claim 2 including, after the step of incubating, removing the non-antibody bound SDS by crystallization, gel filtration or by passage over albumin/Sepharose.

9. The method of claim 3 wherein said detergent is present in a concentration of 0.1%.

10. The method of claim 3 wherein said detergent is present in a concentration of 0.5%.

11. The method of claim 3 wherein said anionic detergent is selected from the group consisting of alkyl sulfates, alkyl aryl sulfates, alkyl aryl sulfonates and alkyl sarcosinates.

12. A method for increasing the solubility of an unconjugated immunoreactive immunoglobulin preparation without substantially affecting the immunoreactivity of the preparation, comprising:
incubating the immunoreactive immunoglobin preparation with an anionic detergent at a concentration between about 0.01% and 1% by weight to volume; and
removing substantially any unbound anionic detergent.

13. The method of claim 11 wherein said anionic detergent is sodium dodecylsulfate.

14. The method of claim 13 wherein said immunoglobin preparation is incubated for 30–60 minutes.

15. The method of claim 14 wherein the step of incubation is carried out at 25° C. or 37° C.

16. The method of claim 13 wherein said detergent is present in a concentration of 0.1%.

17. The method of claim 13 wherein said detergent is present in a concentration of 0.5%.

18. The method of claim 13 wherein said anionic detergent is selected from the group consisting of alkyl sulfates, alkyl aryl sulfates, alkyl aryl sulfonates and alkyl sarcosinates.

19. The method of claim 12 wherein said immunoglobulin preparation is a member of the subclass $IgG_3$.

20. A method for reducing the capability of an immunoreactive antibody, or an immunoreactive antibody conjugate, to bind to a nonspecific receptor without substantially affecting the immunoreactivity of the antibody or antibody conjugate, comprising:
incubating the immunoreactive antibody or immunoreactive antibody conjugate with an anionic detergent at a concentration between about 0.01% and 1% by weight to volume; and
removing substantially any unbound anionic detergent.

21. The method of claim 18 wherein said anionic detergent is sodium dodecylsulfate.

22. The method of claim 20 wherein said antibody or antibody conjugate is incubated for 30–60 minutes.

23. The method of claim 22 wherein the step of incubation is carried out at 25° C. or 37° C.

24. The method of claim 21 wherein said detergent is present in a concentration of 0.1%.

25. The method of claim 21 wherein said detergent is present in a concentration of 0.5%.

26. The method of claim 21 wherein said anionic detergent is selected from the group consisting of alkyl sulfates, alkyl aryl sulfates, alkyl aryl sulfonates and alkyl sarcosinates.

27. The method of claim 20 wherein the receptor is selected from the group consisting of Fc receptors, C3b receptors, C3d receptors, immune complex receptors, carbohydrate receptors and glycoprotein receptors.

28. A method for reducing the toxicity of intact toxin conjugates, comprising:
incubating the toxin conjugate with an anionic detergent at a concentration between about 0.01% and 1% by weight to volume; and
removing substantially any unbound anioinic detergent.

29. The method of claim 25 wherein said anionic detergent is sodium dodecylsulfate.

30. The method of claim 27 wherein said toxin conjugates are incubated for 30–60 minutes.

31. The method of claim 30 wherein the step of incubation is carried out at 25° C. or 37° C.

32. The method of claim 29 wherein said detergent is present in a concentration of 0.1%.

33. The method of claim 29 wherein said detergent is present in a concentration of 0.5%.

34. The method of claim 29 wherein said anionic detergent is selected from the group consisting of alkyl sulfates, alkyl aryl sulfates, alkyl aryl sulfonates and alkyl sarcosinates.

35. The method of claim 28 wherein the intact toxin is abrin.

36. A method for reducing the level of endotoxin activity in biological preparations, comprising:
incubating the biological preparation with an anionic detergent at a concentration between about 0.01% and 1% by weight to volume; and
removing substantially any unbound anioinic detergent.

37. The method of claim 31 wherein said anionic detergent is sodium dodecylsulfate.

38. The method of claim 33 wherein said monoclonal antibody preparation is incubated for 30–60 minutes.

39. The method of claim 38 wherein the step of incubation is carried out at 25° C. or 37° C.

40. The method of claim 37 wherein said detergent is present in a concentration of 0.1%.

41. The method of claim 37 wherein said detergent is present in a concentration of 0.5%.

42. The method of claim 37 wherein said anionic detergent is selected from the group consisting of alkyl sulfates, alkyl aryl sulfates, alkyl aryl sulfonates and alkyl sarcosinates.

43. The method of claim 31 wherein said biological preparation is a monoclonal antibody preparation purified from ascites of BALB/c mice or from monoclonal antibody grown in large scale tissue culture.

* * * * *

UNITED STATES PATENT AND TRADEMARK OFFICE
CERTIFICATE OF CORRECTION

PATENT NO. : 5,151,266

DATED : September 29, 1992

INVENTOR(S) : Morgan, Jr., et al

It is certified that error appears in the above-indentified patent and that said Letters Patent is hereby corrected as shown below:

In column 11, line 14 [claim 1], please change "ananionic" to --an anionic--.

In column 11, line 21 [claim 3], please delete "2" and insert --1-- therefor.

In column 11, line 24 [claim 4], please delete "2" and insert --1-- therefor.

In column 11, line 28 [claim 6], please delete "2" and insert --1-- therefor.

In column 11, line 31 [claim 7], please delete "2" and insert --1-- therefor.

In column 11, line 38 [claim 9], please delete "3" and insert --1-- therefor.

In column 11, line 40 [claim 10], please delete "3" and insert --1-- therefor.

In column 11, line 42 [claim 11], please delete "3" and insert --1-- therefor.

In column 11, line 50 [claim 12], please change "immunoglobin" to --immunoglobulin--.

In column 11, line 56 [claim 13], please delete "11" and insert --12-- therefor.

In column 11, lines 57-58 [claim 14], please change "immunoglobin" to --immunoglobulin--.

In column 12, line 16 [claim 21], please delete "18" and insert --20-- therefor.

UNITED STATES PATENT AND TRADEMARK OFFICE
CERTIFICATE OF CORRECTION

PATENT NO. : 5,151,266
DATED : September 29, 1992
INVENTOR(S) : Morgan, Jr., et al It is certified that error appears in the above-indentified patent and that said Letters Patent is hereby corrected as shown below:

In column 12, line 18 [claim 22], please delete "20" and insert --21-- therefor.

In column 12, line 40 [claim 28], please change "aniolnic" to --anionic--.

In column 12, line 42 [claim 29], please delete "25" and insert --28-- therefor.

In column 12, line 44 [claim 30], please delete "27" and insert --29-- therefor.

In column 12, line 65 [claim 37], please delete "31" and insert --36-- therefor.

In column 12, line 67 [claim 38], please delete "33" and insert --37-- therefor.

In column 14, line 3 [claim 43], please delete "31" and insert --36-- therefor.

Signed and Sealed this

Ninth Day of January, 1996

Attest:

BRUCE LEHMAN

Attesting Officer

Commissioner of Patents and Trademarks